(12) United States Patent
Muzykantov et al.

(10) Patent No.: US 7,674,466 B2
(45) Date of Patent: Mar. 9, 2010

(54) TARGETING AND PROLONGING ASSOCIATION OF DRUGS TO THE LUMINAL SURFACE OF THE PULMONARY VASCULAR ENDOTHELIAL CELLS USING ANTIBODIES THAT BIND TO ICAM-1

(75) Inventors: Vladimir R. Muzykantov, Warwick, PA (US); Juan Carlos Murciano, Sevilla (ES); D. Neil Granger, Shreveport, LA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/234,594

(22) Filed: Sep. 23, 2005

(65) Prior Publication Data

US 2006/0024303 A1    Feb. 2, 2006

Related U.S. Application Data

(63) Continuation of application No. 09/762,023, filed as application No. PCT/US99/17386 on Aug. 2, 1999, now abandoned.

(60) Provisional application No. 60/095,240, filed on Aug. 4, 1998.

(51) Int. Cl.
*A61K 39/00* (2006.01)

(52) U.S. Cl. .............. 424/192.1; 424/133.1; 424/143.1; 424/184.1; 424/193.1; 530/391.7

(58) Field of Classification Search ........................ None
See application file for complete search history.

(56) References Cited

U.S. PATENT DOCUMENTS

| | | | |
|---|---|---|---|
| 5,653,979 | A | 8/1997 | Muzykantov |
| 5,693,762 | A * | 12/1997 | Queen et al. ............ 530/387.3 |
| 6,488,927 | B2 | 12/2002 | Muzykantov |
| 7,041,287 | B2 | 5/2006 | Muzykantov |
| 7,157,087 | B2 | 1/2007 | Muzykantov |
| 7,172,760 | B2 | 2/2007 | Muzykantov |
| 2006/0127386 | A1 | 6/2006 | Muzykantov |
| 2006/0140917 | A1 | 6/2006 | Muzykantov |
| 2007/0065451 | A1 | 3/2007 | Muzykantov |
| 2008/0050389 | A1 | 2/2008 | Muzykantov |

FOREIGN PATENT DOCUMENTS

| | | |
|---|---|---|
| EP | A-0289949 | 11/1988 |
| WO | WO 91/16928 | 11/1991 |
| WO | WO 0007625 A1 * | 2/2000 |

OTHER PUBLICATIONS

Almenar-Queralt et al., Am. J. Pathology, 1995, 147:1278-1288.*
Murciano et al., Blood, 2003 101:3977-3984.*
Gulba et al., Ann. Hematol. 1996, 73 suppl 1:s9-27.*
Walenga et al., Curr Opin Pulm Med, 1997, 3:291-302.*
Bowes et al., "Monoclonal Antibody to the ICAM-1 Adhesion Site Reduces Neurological Damage in a Rabbit Cerebral Embolism Stroke Model", *Exp. Neurology* 1993 119:215-219.
Bowes et al., "Monoclonal antibodies preventing leukocyte activation reduce experimental neurologic injury and enhance efficacy of thrombolytic therapy" *Neurology* 1995 45:815-819.
Imaizumi T., "Effect of Antibodies Against Neutrophil and Endothelial Adhesion Molecules on Reperfusion Injury After Pulmonary Ischemia", *Transpl. Pro.* 1994 26:1851-1854.
Mulligan et al., "Tumor Necrosis Factor α Regulates in Vivo Intrapulmonary Expression of ICAM-1", *Amer. J. Pathol.* 1993 142:1739-1749.
Muzykantov et al.. "Immunotargeting of erythrocyte-bound streptokinase provides local lysis of a fibrin clot", *Biochim. Biophys. Acta.* 1986 884:355-362.
Muzykantov et al., "Endothelial cells internalize monoclonal antibody to angiotensin-converting enzyme", *Amer. J. Pkysiol.* 1996 270:L704-713.
Panes et al., "Regional differences in constitutive and induced ICAM-1 expression in vivo", *Amer. J. Physiol.* 1995 269:H1955-H1964.
Runge et al., "Antibody-enhanced thrombolysis: Targeting of tissue plasminogen activator in vivo", *Proc. Natl. Acad. Sci. USA* 1987 84:7659-7662.
Runge et al., "Conjugation to an Antifibrin Monoclonal Antibody Enhances the Fibrinolytic Potency of Tissue Plasminogen Activator in Vitro", *Biochem.* 1988 27:1153-1157.
Torchilin et al., "Long acting thrombolytic immobilized enzymes", *J. Contr. Rel.* 1985 2:321-330.

(Continued)

*Primary Examiner*—Michael Szperka
(74) *Attorney, Agent, or Firm*—Howson & Howson LLP

(57) ABSTRACT

Methods for targeting and prolonging association of a selected drug to the luminal surface of pulmonary vascular endothelium of an animal are provided wherein a selected drug is administered to an animal in combination with a non-internalizable ICAM-1 antibody which binds to an antigen on the luminal surface of the pulmonary vasculature. This method is particularly useful in dissolution of fibrin clots or prevention of the intravascular coagulation in the pulmonary vasculature.

5 Claims, No Drawings

OTHER PUBLICATIONS

Muro et al., "ICAM-1 recycling in endothelial cells: a novel pathway for sustained intracellular delivery and prolonged effects of drugs" Blood, 105(2):650-658, Jan. 2005.

Muro et al., "Lysosomal enzyme delivery by ICAM-1-targeting nanocarriers bypassing glycosolyation- and clathryn- dependent endocytosis" Molecular Therapy, 13(1):135-41, Jan. 2006.

Von Zastrow et al., "Antagonist-dependent and -independent steps in the mechanism of adrenergic receptor internalization" JBC, 269(28):18448-18452, Jul. 1994.

Muzykantov et al., "Streptavidin facilitates internalization and pulmonary targeting of an anti-endothelial cell antibody (platelet-endothelial cell adhesion molecule 1): a strategy for vascular immunotargeting of drugs", Proc. Natl. Acad. Sci. USA 96(5):2379-2384, Mar. 1999.

Ding et al, Endothelial targeting of a recombinant construct fusing a PECAM-1 single-chain variable antibody fragment (scFv) with prourokinase facilitates prophylactic thrombolysis in the pulmonary vasculature, Blood, Dec. 15, 2005, vol. 106, No. 13, pp. 4191-4198.

Bloemen et al, Adhesion molecules: A new target for immunoliposome-mediated drug delivery, FEBS Letters, Jan. 1995, vol. 357, pp. 140-144.

* cited by examiner

TARGETING AND PROLONGING ASSOCIATION OF DRUGS TO THE LUMINAL SURFACE OF THE PULMONARY VASCULAR ENDOTHELIAL CELLS USING ANTIBODIES THAT BIND TO ICAM-1

This application is a Continuation Application of U.S. patent application Ser. No. 09/762,023 filed Jun. 28, 2001 now abandoned, which is a U.S. National Stage application of PCT/US1999/17386 filed Aug. 2, 1999 which claims the benefit of priority to U.S. Provisional Application Ser. No. 60/095,240, filed Aug. 4, 1998, each of which are herein incorporated by reference in their entirety.

BACKGROUND OF THE INVENTION

Pulmonary vasculature is anatomically predisposed to deposition of fibrin and thromboemboli formed in the vasculature (for example, upon deep vein thrombosis). Both emboli and fibrin lodged in the lung play an important role in the pulmonary and cardiovascular pathology and contribute significantly to morbidity and mortality of disease conditions including, but not limited to, thrombosis, atherosclerosis, deep vein thrombosis, diabetes, adult respiratory distress syndrome, pulmonary embolism, shock and sepsis. Anticoagulants (e.g., heparin) are useful in preventing formation of intravascular fibrin clots, whereas fibrinolytics (e.g., plasminogen activators) are useful for dissolution of fibrin clots. Both anticoagulants and fibrinolytics, however, undergo inactivation and elimination from the bloodstream. This restricts their applicability for treatment of pulmonary embolism. Administration of large doses and/or multiple injections of a drug to compensate for elimination/inactivation impose inconvenience in treatment and high risk of harmful side effects. Uncontrolled bleeding is an example of such side effects of prolonged administration or a large dose of anticoagulants or fibrinolytics.

Augmentation of anticoagulant or/and fibrinolytic potential of the luminal surface of endothelial cells lining pulmonary vessels thus represents an important therapeutic strategy for treatment or/and prevention of disease conditions associated with or manifested by pulmonary embolism and fibrin deposition. Because these therapeutics must have access to the blood components in order to control coagulation or activate fibrinolysis, a requirement for such a strategy is that the anticoagulant or fibrinolytic agent be associated for a prolonged time with the luminal surface of the pulmonary endothelium.

One approach to attain this objective is to conjugate a drug to an antibody against surface endothelial molecules. This conjugation provides selective delivery, also referred to herein as targeting, of a drug to endothelium and prolonged association of a drug with endothelium. Therapeutic enzymes and genetic material conjugated to such antibodies have been demonstrated to bind to the endothelial cells in vitro and in vivo after injection in animals. Since the lungs contain approximately 30% of the total amount of endothelial cells in the body and receive a whole cardiac output of venous blood, antibodies against endothelial antigens tend to accumulate in the lung after intravenous injection. For example, Kennel et al. have described an antibody against thrombomodulin which recognizes endothelial surface in vivo, accumulates in the pulmonary vasculature and is capable of delivery of conjugated liposomes to the pulmonary endothelium (Kennel et al. 1990 *Nucl. Med. Biol.* 17:193-100; Trubetskoy et al. 1992 *Biochim. Biophys. Acta* 1131:311-313). An antibody against angiotensin-converting enzyme (ACE) has been described which possesses very similar properties (Danilov et al. 1991 *Lab. Invest.* 64:118-124). Therapeutic enzymes such as catalase, superoxide dismutase and plasminogen activators conjugated with ACE antibody have been demonstrated to accumulate in the lungs after intravascular injection (Muzykantov et al. 1996 *Proc. Nat'l Acad. Sci. USA* 93:5213-5218; Muzykantov et al. 1997 *J. Pharm. Exp. Therap.* 279:1026-1034). In addition, an antibody against E-selectin has been described which binds to and delivers liposomes to the cytokine-activated endothelium in cell culture (Spragg et al. 1997 *Proc. Nat'l Acad. Sci. USA* 94:8795-8800). A PECAM antibody conjugated with streptavidin has also been recently described which provides an effective carrier for delivery of drugs to the endothelium (Muzykantov et al. 1998 *Am. J. Resp. Crit. Care Med.* 157:A203).

However, endothelial cells internalize antibodies against thrombomodulin (Muzykantov et al. 1997 *Circulation* 96:I43-44), ACE (Muzykantov et al. 1996 *Am. J. Physiol.* 270:L704-713), E-selectin (Spragg et al. 1997 *Proc. Nat'l Acad. Sci. USA* 94:8795-8800) and anti-PECAM/streptavidin complex (Muzykantov et al. 1998 *Am. J. Resp. Crit. Care Medicine* 157:A203). Thus, while these carriers provide intracellular delivery, a feature which may be useful for targeting of genes and some other therapeutic agents, anticoagulants or fibrinolytics must escape internalization and remain on the luminal surface in order to control blood components. Accordingly, these carrier antibodies are of limited use in the delivery of anticoagulants, fibrinolytics or other drugs wherein their therapeutic action is localized to the blood.

An ICAM-1 monoclonal antibody, mAb 1A29 has also been described which accumulates in rat lungs following i.v. injection. Conjugation of catalase to this ICAM-1 monoclonal antibody via a streptavidin-biotin crosslinker resulted in accumulation of the anti-ICAM-1 conjugated catalase in the lung and protection of the lung from damage by extracellular oxidants (Muzykantov et al. *Am. J. Resp. Crit. Care Medicine* 1997 155(4):p. A187). Radiolabeled mAb 1A29 has also been shown to accumulate in the vasculature challenged with pro-inflammatory agents TNF and endotoxin (Mulligan et al. 1993 *Am. J. Pathol.* 142:1739-1749). In addition, this antibody has been shown to react with normal endothelial cells in the rat vasculature and that injection of TNF or endotoxin stimulates endothelial binding of mAb 1A29 (Panes et al. 1995 *Am. J. Physiol.* 269:H1955-1964). This antibody has also been shown to attenuate vascular injury induced by activated leukocytes via blocking of their adhesion to the endothelial cells.

It has now been found that monoclonal antibodies against the endothelial surface antigen ICAM-1 bind effectively to the endothelial cells without subsequent internalization. Conjugation of a drug to an non-internalizable antibody such as the ICAM-1 monoclonal antibody which binds to an antigen on the luminal surface of the pulmonary vasculature provides a useful means for targeted delivery and retention of the drug on the luminal surface, or blood compartment, of the pulmonary vasculature.

SUMMARY OF THE INVENTION

An object of the present invention is to provide a method for targeting and prolonging association of drugs, the therapeutic action of which must be localized in the blood compartment of the pulmonary vasculature, to the luminal surface of either normal or inflammation-affected pulmonary vascular endothelium, which comprises utilization of a non-internalizable antibody which binds to an antigen on the luminal surface of the pulmonary vasculature, for example an anti- ICAM-1 antibody such as anti-ICAM-1 mAb 1A29, as an affinity carrier or a membrane anchor for the targeting and retention of the drugs on the luminal surface of the endothelium.

Another object of the present invention is to provide a method of administration of a drug, the therapeutic action of which must be localized in the blood compartment of the pulmonary vasculature which comprises either: I) conjugation of a selected drug with a non-internalizable antibody which binds to an antigen on the luminal surface of the pulmonary vasculature, for example an anti-ICAM-1 antibody such as anti-ICAM-1 mAb 1A29, leading to formation of a "non-internalizable antibody/drug" complex and systemic administration of the said complex to an animal; or ii) stepwise systemic administration to an animal of a non-internalizable antibody which binds to an antigen on the luminal surface of the pulmonary vasculature followed by systemic administration of a drug chemically modified in the way that allows the drug to recognize and bind to the non-internalizable antibody bound to the luminal surface to avoid internalization.

Another object of the present invention is to provide a method for dissolution of fibrin clots or attenuation of the intravascular coagulation in the lung of an animal which comprises systemically administering to the animal a fibrinolytic or anticoagulant agent in combination with a non-internalizable monoclonal antibody which binds to an antigen on the luminal surface of the pulmonary vasculature.

DETAILED DESCRIPTION OF THE INVENTION

ICAM-1 (InterCellular Adhesion Molecule-1) is a transmembrane protein anchored in the plasma membrane of several cell types, including endothelial cells. ICAM-1 is present on the surface of normal (non-stimulated) endothelium. Inflammatory agents cause elevation of ICAM-1 levels on the endothelial surface. Thus, inflammation-engaged endothelium possesses even more binding sites for ICAM-1 antibody than normal endothelium.

Monoclonal antibodies against ICAM-1 have been demonstrated to be useful as carriers of agents to the pulmonary endothelium. Accordingly, studies were performed to ascertain the usefulness of these anti-ICAM-1 antibodies in delivery of drugs such as fibrinolytics and anticoagulants. Anti-ICAM-1 mAb 1A29, a monoclonal antibody serving as an example in the present invention which is a mouse IgG1 class monoclonal antibody reacting with rat ICAM-1, was used in these studies. This antibody is commercially available from a number of vendors including PharMingen (San Diego, Calif.), Endogen, Inc. (Boston, Mass.) and Serotec Ltd (United Kingdom). Since lack of internalization is an obligatory for the therapeutic action of fibrinolytics and anticoagulants, studies were performed to determine how endothelial cells in cell culture or in the lung blood vessels internalize radiolabeled mAb 1A29. These experiments demonstrated that unlike antibodies to other endothelial antigens, endothelial cells internalize anti-ICAM-1 extremely poorly.

For example, in cell culture, internalization of $^{125}$I-mAb 1A29 did not exceed 5-10%. In contrast, $^{125}$I-mAb against other endothelial antigens such as thrombomodulin and ACE displayed 60-80% internalization.

In addition, pulmonary uptake of anti-ICAM-1 is independent of the temperature thus indicating that this antibody is not internalized. Uptake of $^{125}$I-mAb 1A29 in the isolated perfused rat lung was 18.7±3.2% at 37° C. and 18.1±3.3% at 4° C. In contrast, pulmonary uptake of $^{125}$I-mAb against ACE was twice as low at 4° C. as compared to 37° C. (Muzykantov et al. 1996 *Am. J. Physiol.* 270:L704-713).

Further, experiments conducted to evaluate whether mAb 1A29 associated with the endothelial cells disappears from the luminal surface in the lung showed that in sharp contrast to anti-ACE and other known carrier antibodies, anti-ICAM-1 is bound to the external surface of the pulmonary endothelial cells for a prolonged time and does not disappear from the lumen. In these experiments, rat lungs were perfused with biotinylated mAb 1A29 (b-mAb 1A29) and after elimination of non-bound antibody consequently perfused $^{125}$I-streptavidin in the lungs. Pulmonary uptake of $^{125}$I-streptavidin was at the same level when streptavidin was added to the perfusion either 5 or 60 minutes after elimination of b-mAb 1A29. In contrast, it has been shown that consequent uptake of $^{125}$I-streptavidin decreases dramatically within an hour after elimination of the biotinylated anti-ACE from the perfusate, thus indicating that b-anti-ACE disappears from the luminal surface.

Taken together, these results indicate that endothelial cells effectively bind anti-ICAM-1 antibodies such as mAb 1A29, yet do not internalize this carrier. Accordingly, drugs targeted to endothelial cells by anti-ICAM-1 will be exposed to the vascular lumen for a prolonged period of time and, therefore, will able to more effectively interact with plasma protein thus regulating coagulation and fibrinolysis.

Pulmonary uptake of fibrinolytics, namely, $^{125}$I-tPA and $^{125}$I-streptokinase conjugated with anti-ICAM-1 mAb 1A29, in the perfused rat lungs and after injection in vivo in rats was evaluated. As Table 1 shows, antibody-conjugated fibrinolytics, but not control IgG-conjugated enzymes accumulate in the rat lungs in both models, thus indicating that anti-ICAM-1 antibody indeed provides delivery of therapeutics to the luminal surface of the pulmonary vascular endothelium.

TABLE 1

Pulmonary uptake of radiolabeled therapeutic enzymes conjugated to either control IgG or to anti-ICAM-1 mAb 1A29.

|  | Carrier | Streptokinase | tPA |
| --- | --- | --- | --- |
| Perfused lung | IgG | 1.3 ± 0.7 | 1.6 ± 0.4 |
| Perfused lung | anti-ICAM | 12.4 ± 1.7 | 15.3 ± 1.6 |
| Lung, in vivo | IgG | ND | 0.22 ± 0.1 |
| Lung, in vivo | anti-ICAM | ND | 6.1 ± 0.7 |

Data in Table 1 are presented as % of injected dose per gram of the lung tissue, M±SD, n=3. Radioactivity in the lung was determined 1 hour after start of the perfusion or after intravenous injection in intact anesthetized rats.

Further, subsequent perfusion of $^{125}$I-tPA/streptavidin complex 60 minutes after accumulation of biotinylated mAb 1A29 in the lungs provided pulmonary uptake of 17.5±2.7% of $^{125}$I-tPA. In a control experiment, in the absence of the first step of the targeting (i.e., without perfusion of biotinylated mAb 1A29) uptake of $^{125}$1I-tPA was equal to 0.7±0.2%, thus demonstrating the specificity of the targeting to b-anti-ICAM-1 attached to the pulmonary endothelium. Comparison of the result of step-wise targeting described above (17.5±2.7%) with that of direct targeting (15.3±1.6%, see Table 1) provides additional evidence that endothelial cells in the lung do not internalize mAb 1A29 as step-wise targeting would clearly be compromised by disappearance of b-mAb 1A29 from the lumen.

The functional activity of tPA targeted to the pulmonary endothelium via an anti-ICAM-1 monoclonal antibody was also evaluated. In these experiments, isolated rat lungs were perfused for 1 hour with 100 μg of mAb 1A29/tPA or IgG/tPA or with buffer. After elimination of non-bound material, lung tissue homogenates were prepared. Samples of lung homogenates were added to radiolabeled fibrin clot and incubated for 90 minutes at 37° C. Homogenate obtained from lungs perfused with conjugate-free buffer induced 6.5±1.0% fibrinolysis (background level). The homogenate obtained from the lungs perfused with IgG/tPA complex induced 9.2±2.5% fibrinolysis. This value is not significantly different from the background fibrinolysis level. In a sharp contrast, homogenate obtained from the lungs perfused with anti-ICAM-1/tPA complex induced 21.2±3.9 fibrinolysis. Thus, anti-ICAM-1-directed targeting of tPA to the luminal surface of the pulmonary endothelium markedly enhances fibrinolytic activity of the lung vasculature. Further, immunotargeting of tPA (or other plasminogen activators) will augment local fibrinolytic potential of endothelium in the focus of the pulmonary vasculature due to local generation of plasmin.

Accordingly, administration of a non-internalizable antibody such as anti-ICAM-1 antibody in combination with a selected drug, the therapeutic action of which must be localized in the blood compartment of the pulmonary vasculature, provides a useful means for targeting and prolonging association of the drug to the luminal surface of either normal or inflammation-affected pulmonary vascular endothelium.

By "non-internalizable antibody" it is meant an antibody which binds to an antigen on the luminal surface of the pulmonary vasculature such as the anti-ICAM-1 antibody, mAb 1A29, which is determined not to be internalized by cultured human endothelial cells as described in Example 2 and/or is shown to be temperature independent in pulmonary uptake experiments in isolated lung perfusions as described in Example 3. Non-internalizable antibodies other than the anti-ICAM-1 antibody described herein which are also useful in the instant invention can thus be identified routinely by those of skill in the art in accordance with teachings provided herein.

By "selected drug" in the present invention, it is meant to include any therapeutic agent, the therapeutic action of which must be localized in the blood compartment of the pulmonary vasculature. Examples include, but are not limited to fibrinolytics including plasminogen activators and anticoagulants.

By "prolonging association", it is meant that the drug when administered in combination with a non-internalizable antibody such as anti-ICAM-1 antibody undergoes slower inactivation and/or elimination from the bloodstream as compared to the same drug administered alone.

By "in combination" it is meant that a selected drug is administered either as a non-internalizable antibody/drug complex or in a stepwise manner wherein the non-internalizable antibody is administered first followed by administration of the selected drug. Thus, in one embodiment, a selected drug can be conjugated to a non-internalizable antibody to form an non-internalizable antibody/drug complex by a number of different methods well known to those of skill in the art. For example, conjugation of anti-ICAM-1 to a selected drug such as a plasminogen activator may be performed using a homo-bifunctional cross-linking agent. Such cross-linking agents offer conjugation of two proteins via chemical modification of the same functional groups on both proteins. Since all proteins contain amino groups, this class of cross-linkers usually produces intermolecular complexes by cross-linking of their amino groups (Sakharov et al. 1988 *Thrombosis Res.* 49:481-488). Introduction of disulfide groups in two proteins by incubation with equimolar amounts of N-succinimidyl-3-(2-pyridildithio)propionate (SPDP) followed by reduction of the disulfide groups on one of the proteins also allows for conjugation of the two proteins (Cavallaro et al. 1993 *J. Biol. Chem.* 268:23186-23190). The hetero-bifunctional cross-linking agent, m-maleimidobenzoic acid N-hydroxysuccinimide ester can also be used for conjugating an SPDP-treated plasminogen activator with any protein including anti-ICAM-1 or, vice versa, SPDP-treated anti-ICAM-1 with a plasminogen activator. A selected drug can also be coupled with the antibody using a bi-functional antibody chimera possessing affinity for both the selected drug and the antibody. In a preferred embodiment, streptavidin-biotin cross-linking is used. In this embodiment, both the antibody and selected drug are modified with biotin ester which allows for further intermolecular conjugation of the biotinylated molecules by streptavidin. Streptavidin-mediated cross-linking of biotinylated proteins is a widely used biochemical method. Further, as demonstrated herein, the enzymatic activity of tPA is not reduced in the course of biotinylation, conjugation with streptavidin and with biotinylated anti-ICAM-1. In addition, the ability of the antibody to specifically target the lung is not altered by this process.

In another embodiment, the selected drug is chemically modified to recognize and bind a non-internalizable antibody such as anti-ICAM-1 antibody associated with or bound to the luminal surface of the endothelium. In this embodiment, referred to herein as step-wise systemic administration, biotinylated non-internalizable antibody is systemically administered to the animal so that the antibody binds to a specific antigen on the luminal surface of the pulmonary vasculature. The selected chemically modified drug is then systemically administered to the animal so that the selected drug binds to the non-internalizable antibody associated with the luminal surface thereby avoiding internalization. For example, the plasminogen activator, tPA, has been chemically conjugated with streptavidin, a molecule recognizing a biotinylated anti-ICAM-1 antibody associated with endothelial surface. Thus tPA/streptavidin complex binds to endothelium-bound anti-ICAM antibody.

Administration of a selected drug in combination with a non-internalizable antibody is particularly useful in dissolution of fibrin clots or prevention of the intravascular coagulation in the lung. In this embodiment, it is preferred that the selected drug be a fibrinolytic agent, preferably a plasminogen activator, or an anticoagulant such as chemically modified heparin, hirudin or recombinant thrombomodulin.

By "systemic administration" it is meant to include intravenous, intraarterial injections and infusions, as well as local delivery via a vascular catheter into selected vascular bed (for example, pulmonary artery).

By "animal" it is meant to include mammals, most preferably humans.

The following nonlimiting examples are provided to further illustrate the present invention.

EXAMPLES

Example 1

Biotinylation, Radiolabeling of Proteins, and Preparation of the Conjugates

Biotin ester, 6-biotinylaminocaproic acid N-hydroxysuccinimide ester (BxNHS) was dissolved in 100% dimethylformamide to a final concentration of 10 mM or 1 mM. Control mouse IgG and anti-ICAM-1 mAb 1A29 were biotinylated at ten-fold molar excess of BxNHS. Eight μl of fresh 1 mM BxNHS were added to 100 μl of antibody solution (1 mg/ml in borate buffered saline, BBS, pH 8.1). After a 1 hour incubation on ice, an excess of non-reacted BxNHS was eliminated by overnight dialysis. Streptokinase and tPA were biotinylated by the same reagent at 10-fold molar excess of BxNHS, as described above. Biotinylated antibodies, b-streptokinase, b-tPA or streptavidin were radiolabeled with $^{125}$Iodine using Iodogen-coated tubes according to the manufacturer's recommendations (Pierce). Incubation of 100 µg of a biotinylated protein and 100 µCi of Sodium $^{125}$Iodide in a tube coated with 100 µg of Iodogen for 20 minutes on ice yields streptavidin with a specific radioactivity of approximately 500 cpm per ng. An excess of iodine was eliminated by dialysis. More than 95% of radiolabeled proteins were precipitable by TCA.

Tri-molecular heteropolymer complexes b-tPA/SA/b-IgG, b-tPA/SA/b-anti-ICAM-1, b-streptokinase/SA/b-IgG and b-streptokinase/SA/b-anti-ICAM-1 were prepared by a two-step procedure. Specifically, at the first step, streptavidin (SA) and b-tPA were mixed at a molar ratio equal to 2, in order to form bi-molecular complexes b-tPA/SA. Accordingly, 10 µl of BBS containing 10 µg of radiolabeled b-tPA was mixed with 10 µl of BBS containing 20 µg of streptavidin and incubated for 1 hour on ice. The mixture was then divided into two 10 µl portions. To the first portion was added 15 µl of BBS containing 20 µl of biotinylated anti-ICAM-1. To the second portion was added 15 µl of BBS containing 20 µg of control IgG. These mixtures were then incubated for two hours on ice, in order to form tri-molecular conjugates b-catalase/SA/b-anti-ICAM or b-catalase/SA/b-IgG. The same procedure has been utilized to generate tri-molecular complexes b-streptokinase/SA/b-IgG, b-streptokinase/SA/b-anti-ICAM.

Example 2

Interaction of Radiolabeled Antibodies with Cultured Human Endothelial Cells

Cultivated cells (HUVEC) were cultured in gelatin-coated plastic dishes ("Falcon") using Medium 199 with Earle's salts supplemented with 10% fetal calf serum, 200 µg/ml endothelial growth factor from human brain and 100 µg/ml heparin, 2 mM glutamine, 100 mU/ml penicillin and 100 µg/ml streptomycin. Cells were subcultivated from first to third passage by treatment with 0.05% trypsin/0.02% EDTA mixture.

To determine the internalization of antibodies by the endothelium, cells were incubated with 300 µl of culture medium containing 1 µl $^{125}$I-anti-ICAM for 90 minutes at 37° C. After washing to remove unbound radioactivity, cells were incubated with 50 mM glycine, 100 mM NaCl, pH 2.5 (15 minutes at room temperature) to release surface associated antibody. There was no detectable cell detachment after treatment with glycine buffer as determined by light microscopy. After collection of the glycine eluates, cells were detached by incubation with standard trypsin/EDTA solution. Surface associated radioactivity (i.e., radioactivity of the glycine eluates) and cell associated radioactivity (i.e., radioactivity of trypsin/EDTA extracts) were determined in a gamma counter. Percent of internalization was calculated as %=(total radioactivity−glycine eluted)×100/total radioactivity.

Example 3

Temperature Dependence of Pulmonary Uptake of Anti-ICAM-1

Sprague-Dawley male rats, weighing 170-200 grams, were anesthetized with sodium pentobarbital, 50 mg/kg, i.p., and prepared for isolated lung perfusion using recirculating perfusate. The trachea was cannulated and lungs were ventilated with a humidified gas mixture (Airco Inc., Philadelphia, Pa.) containing 5% $CO_2$ and 95% air. Ventilation was performed using a SAR-830 rodent ventilator (CWE Inc., Ardmore, Pa.) at 60 cycles/minute, 2 ml tidal volume, and 2 cm $H_2O$ end-expiratory pressure. The thorax was then opened and a cannula was placed in the main pulmonary artery through the transected heart. The lungs were isolated from the thorax and initially perfused in a non-recirculating manner for a 5 minute equilibration period, in order to eliminate blood from the pulmonary vascular bed. Then lungs were transferred to the water-jacketed perfusion chamber maintained at 37° C. or 60° C. Perfusion through the pulmonary artery was maintained by a peristaltic pump at a constant flow rate of 10 ml/minutes. The perfusate (45 ml per lung) was Krebs-Ringer buffer. (KRB, pH 7.4), containing 10 mM glucose and 3% fatty acid-free BSA (KRB-BSA). Perfusate was filtered through a 0.4 µm filter prior to perfusion to eliminate particulates. To quantitate antibody binding, 1 µg of $^{125}$-labeled anti-ICAM-1 antibody 1A29 was added to the perfusate. Perfusate circulated for 60 minutes at either 37° C. or 4° C. Then non-bound material was eliminated by 5 minutes non-recirculating perfusion of antibody-free KRB-BSA. Radioactivity in the lungs was measured in a gamma-counter and expressed as a percentage of perfused radioactivity per gram of lung tissue (% ID/g).

Example 4

Rat Lung Perfusions with Biotinylated mAb 1A29

Perfusion of isolated rat lungs was performed as above. At the first step, 10 µl of non-labeled biotinylated anti-ICAM-1 antibody was added to the perfusate and circulated for 30 minutes at 37° C., to allow for antibody binding with the pulmonary endothelium. Thereafter, non-bound antibody was eliminated as above and perfusate was replaced with antibody-free KRB-BSA. Lungs were further perfused for either 5 minutes (to minimize antibody internalization) or 60 minutes at 37° C. (to allow for antibody internalization). At the indicated time, 1 µg of $^{125}$I-labeled streptavidin was perfused for 15 minutes with recirculating perfusion at 37° C. followed by 5 minutes with non-recirculating perfusion with KRB-BSA to eliminate non-bound material. Radioactivity in the lungs was measured in a gamma-counter and expressed as a percentage of perfused radioactivity per gram of lung tissue (% ID/g).

Example 5

Pulmonary Uptake of $^{125}$I-tPA and $^{125}$I-Streptokinase Conjugated with anti-ICAM-1 mAb 1A29 in Perfused Rat Lungs To study pulmonary uptake of radiolabeled preparations in blood-free buffer, 0.5 ml of saline containing 1 µg of radiolabeled b-streptokinase or b-tPA conjugated with anti-ICAM-1 antibody 1A29 was added to the perfusate and circulated in the isolated rat lungs for 1 hour at 37° C., as described above. Control lungs were perfused with complexes containing b-IgG instead of b-anti-ICAM-1. After a one hour perfusion, non-bound material was eliminated and lung-associated radioactivity was determined as above.

Example 6

Pulmonary Uptake of $^{125}$I-tPA and $^{125}$I-Streptokinase Conjugated with anti-ICAM-1 mAb 1A29 After Injection in vivo in Rats To study biodistribution of radiolabeled preparations in rats, an injection of 0.5 ml of saline containing 1 µg of radiolabeled b-streptokinase or b-tPA conjugated with anti-ICAM-1 antibody 1A29 was made into the tail vein under anesthesia. Control animals were injected with complexes containing b-IgG instead of b-anti-ICAM-1. Animals were sacrificed by exsanguination 60 minutes after injection. Internal organs were washed with saline to remove blood and radioactivity in tissues was determined in a Rack-Gamma counter. The data were calculated as mean±standard error (M±SE). Statistical comparisons were made using one-way analysis of equal variance (ANOVA) followed by Student-Newman-Keuls Method. The level of statistical significance was taken as $p<0.05$.

Example 7

Functional Activity of tPA in Isolated Rat Lungs

To characterize functional activity of tPA conjugated with anti-ICAM antibody, 0.5 ml of saline containing 1 µl of b-tPA conjugated with anti-ICAM-1 antibody 1A29 was added to the perfusate and circulated in the isolated rat lungs for 1 hour at 37° C., as described above. Control lungs were perfused with complexes containing b-IgG instead of b-anti-ICAM-1. After a one hour perfusion, non-bound material was eliminated and lung homogenates were prepared. To test fibrinolytic activity of the homogenates, radiolabeled fibrin clot was prepared by addition of 50 µl of thrombin solution (1 µg/ml in saline) to a solution of radiolabeled human fibrinogen (3 mg/ml in KRB). Immediately after thrombin addition, aliquots of the solution (300 µl) were made and allowed to polymerize (60 minutes at room temperature). This procedure provides standard fibrin clots containing radiolabeled fibrin. Saline (1 ml) containing 50 ml of the homogenates prepared from lungs perfused with either b-tPA/SA/b-anti-ICAM or b-tPA/SA/b-IgG complexes (see above) was added to fibrin clots. After a 2 hour incubation at 37° C., radioactivity in the supernatants was determined. Percent of fibrinolysis was expressed as percent of the radioactivity in the supernatants (i.e., radioactivity of the products of fibrin degradation) to the total radioactivity of fibrin clots.

What is claimed is:

1. A method comprising administering to an animal a composition comprising a plasminogen activator conjugated to an ICAM-1 antibody prior to formation of fibrin, blood clotting or thromboembolism in the pulmonary vasculature.

2. The method according to claim 1, wherein said administering causes generation of plasmin in blood in the pulmonary vasculature.

3. The method according to claim 1, wherein the animal is a human.

4. A method comprising administering to an animal a composition comprising a plasminogen activator conjugated to an anti-ICAM-1 antibody to inhibit effects of blood clotting and thromboembolism occlusion in the pulmonary vasculature of the animal.

5. The method according to claim 4, wherein the animal is a human.

* * * * *